United States Patent [19]

Weinberg et al.

[11] 4,143,057

[45] Mar. 6, 1979

[54] COORDINATION COMPLEXES AS CATALYSTS

[75] Inventors: Kurt Weinberg, Upper Saddle River, N.J.; Gordon C. Johnson, Armonk, N.Y.

[73] Assignee: Union Carbide Corporation, New York, N.Y.

[21] Appl. No.: 773,001

[22] Filed: Feb. 28, 1977

[51] Int. Cl.$^2$ .................... C07F 7/30; C07F 7/28; C07F 7/22; C07F 7/00

[52] U.S. Cl. .................... 260/429 R; 252/429 R; 252/431 P; 260/429.3; 260/429.5; 260/429.7; 260/429.9; 260/435 R; 260/446; 260/447; 528/279; 528/281; 528/283; 528/285

[58] Field of Search ............ 252/429 R, 431 P; 260/75 R, 429.5, 429.7, 429.3, 429 R, 446, 435, 447, 429.9

[56] References Cited

U.S. PATENT DOCUMENTS

| | | | |
|---|---|---|---|
| 2,465,319 | 3/1949 | Whinfield et al. | 260/75 C |
| 2,823,218 | 2/1958 | Speier et al. | 260/448.2 |
| 2,843,615 | 7/1958 | Linville | 260/448.8 |
| 2,970,150 | 1/1961 | Bailey | 260/348 |
| 3,067,229 | 12/1962 | Fekete | 260/448.2 |
| 3,122,581 | 2/1964 | Pike | 260/448.8 |
| 3,248,409 | 4/1966 | Bluestein | 260/414 |
| 3,355,439 | 11/1967 | Welch et al. | 260/446 X |
| 3,397,216 | 8/1968 | Welch et al. | 260/429.5 |
| 3,412,125 | 11/1968 | Welch et al. | 260/446 |
| 3,501,403 | 3/1970 | Jacques et al. | 252/46.7 |
| 3,546,179 | 12/1970 | Koller | 260/75 |
| 3,652,503 | 3/1972 | Hewertson | 252/429 R UX |
| 3,726,809 | 4/1973 | Allum et al. | 252/431 P |
| 3,775,452 | 11/1973 | Karstedt | 260/429 R |
| 3,832,404 | 8/1974 | Allum | 252/431 P X |
| 3,856,837 | 12/1974 | Chandra | 260/429 R |
| 3,907,852 | 9/1975 | Oswald et al. | 252/429 R X |
| 3,987,009 | 10/1976 | Young | 252/431 C X |
| 4,083,803 | 4/1978 | Oswald | 252/431 P |

*Primary Examiner*—Helen M. S. Sneed
*Attorney, Agent, or Firm*—Francis M. Fazio

[57] ABSTRACT

A process for producing polyesters and copolyesters, useful for making films and fibers, by the polycondensation of dicarboxylic acids and aliphatic glycols using coordinations complexes of metal halides and silicon compounds as catalysts.

15 Claims, No Drawings

COORDINATION COMPLEXES AS CATALYSTS

BACKGROUND OF THE INVENTION

The production of polyesters and copolyesters of dicarboxylic acids and aliphatic glycols has been carried out commercially for many decades. Among the earliest disclosures relating to this technology is the disclosure in U.S. Pat. No. 2,465,319, issued Mar. 22, 1949. Since this disclosure many variations have been made in the process and many catalysts have been discovered and patented. On Dec. 8, 1970, there issued U.S. Pat. No. 3,546,179, which is directed to the use of compounds containing both the silicon and phosphorus atoms in the molecule as catalysts.

SUMMARY OF THE INVENTION

It has now been found that coordination complexes of a metal halide and a silicon compound, as hereinafter defined, are excellent polyesterification catalyst complexes for the production of polyesters and copolyesters useful for making films, fibers and other shaped articles.

DESCRIPTION OF THE INVENTION

In the production of polyesters and copolyesters the reaction is generally considered a dual or two stage reaction. In the first stage esterification or transesterification occurs and in the second stage polycondensation occurs. This invention is concerned with novel polyesterification catalyst compositions and processes for producing polyesters.

The novel catalyst compositions of this invention are coordination complexes of (A) a metal halide and (B) a silicon compound, as hereinafter more fully defined. The use of our catalyst complexes or compositions results in a shorter reaction period, and the production of polyesters and copolyesters of high degrees of polycondensation that are characterized by high melting point, high elongation at break, good tensile strength, high degree of whiteness, and a good stability to heat and light.

The first stage esterification or transesterification reaction is carried out in the traditional manner by heating the mixture at from about 150° C. to about 270° C., preferably from about 175° C. to about 250° C. During this stage any of the well-known esterification or transesterification catalysts can be used, illustrative thereof one can mention zinc acetate, manganese acetate, cobaltous acetate, zinc succinate, zinc borate, magnesium methoxide, sodium methoxide, cadmium formate, and the like. The concentration thereof is that conventionally used, namely from about 0.001 to about one percent by weight, based on the weight of dicarboxylic acid compound charged. It is preferably from about 0.005 to about 0.5 percent by weight and more preferably from about 0.01 to about 0.2 percent by weight.

In the second stage, or the polycondensation, the novel coordination complex catalysts of this invention are useful. These novel coordination complex catalysts comprise two essential components. The first component is a metal halide and the second component is one or more of the hereinafter defined silicon compounds.

The metal halides used to produce the coordination complexes useful as catalysts are the halides of the metals titanium, zirconium, zinc, germanium, tin, lead, antimony and bismuth. Illustrative of suitable metal halides one can include the di-, tri- and tetra-bromides, chlorides, fluorides and iodides of titanium and zirconium; the di-bromides, chlorides, fluorides and iodides of zinc; the di- and tetra-bromides, chlorides, fluorides and iodides of germanium, tin and lead including the mixed bromide-chlorides, bromide-iodides and chloride-iodides of tin; the tri- and penta-bromides, chlorides, fluorides and iodides of antimony; and the tri- and tetra-bromides, chlorides, fluorides and iodides of bismuth. These metal halides are well known to the average chemist and are fully enumerated in chemical handbooks to the extent that specific naming thereof is not necessary herein to enable one skilled in the art to know chemical names of the specific metal halides per se; see the Handbook of Chemistry and Physics, Chemical Rubber Publishing Co., publisher.

In producing the coordination complexes useful as catalysts, the molar ratio of metal halide to silicon compound in the coordination complex can vary from about 1:0.5 to about 1:10; preferably from about 1:1 to about 1:7, and most preferably from about 1:1 to about 1:2.

In the polycondensation reaction the coordination catalyst complex is used at a concentration of from 0.01 to 0.2 weight percent, or higher, based on the weight of dicarboxylic acid compound charged, preferably from 0.02 to 0.06 weight percent. Any catalytically effective concentration can be employed. As used in this application the term "dicarboxylic acid compound" means both the free dicarboxylic acids and the esters thereof.

The dicarboxylic acid compounds used in the production of polyesters and copolyesters are well known to those skilled in the art and illustratively include terephthalic acid, isoterephthalic acid, p,p'-diphenyldicarboxylic acid, p,p'-dicarboxydiphenyl ethane, p,p'-dicarboxydiphenyl hexane, p,p'-dicarboxydiphenyl ether, p,p'-dicarboxyphenoxy ethane, and the like, and the dialkyl esters thereof that contain from 1 to about 5 carbon atoms in the alkyl groups thereof.

Suitable aliphatic glycols for the production of polyesters and copolyesters are the acyclic and alicyclic aliphatic glycols having from 2 to 10 carbon atoms, especially those represented by the general formula $HO(CH_2)_pOH$, wherein p is an integer having a value of from 2 to about 10, such as ethylene glycol, trimethylene glycol, tetramethylene glycol, pentamethylene glycol, decamethylene glycol, and the like.

Other known suitable aliphatic glycols include 1,4-cyclohexanedimethanol, 3-ethyl-1,5-pentanediol, 1,4-xylylene glycol, 2,2,4,4-tetramethyl-1,3-cyclobutanediol, and the like. One can also have present a hydroxylcarboxyl compound such as 4-hydroxybenzoic acid, 4-hydroxyethoxybenzoic acid, or any of the other hydroxylcarboxyl compounds known as useful to those skilled in the art.

It is also known that mixtures of the above dicarboxylic acid compounds or aliphatic glycols can be used and that a minor amount of the dicarboxylic acid component, generally up to about 10 mole percent, can be replaced by other acids or modifiers such as adipic acid, sebacic acid, or the esters thereof, or with a modifier that imparts improved dyeability to the polymers. In addition one can also include pigments, delusterants or optical brighteners by the known procedures and in the known amounts.

The polycondensation reaction is generally carried out at a temperature of from about 225° C. to about 325° C., preferably from about 250° C. to about 290° C. at reduced pressure and under an inert atmosphere. These traditional reaction conditions are well known to those skilled in the art.

The silicon compounds that are used in conjunction with the metal halide to produce the coordination complex catalyst of this invention are represented by the following generic formulas:

$$W-(COOC_nH_{2n})_m-\underset{\underset{R'}{|}}{\overset{\overset{R}{|}}{Si}}-R'' \qquad (I)$$

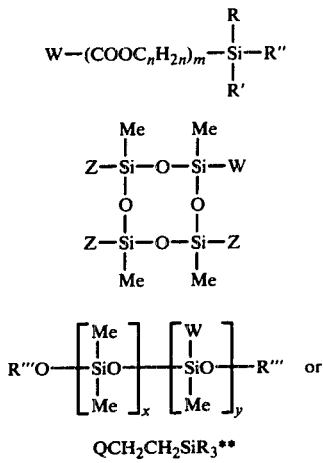

$$QCH_2CH_2SiR_3^{**} \qquad (IV)$$

wherein
W is $CH_2=CX-$ or

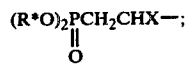

X is hydrogen or methyl and is methyl only when m is one;
R* is alkyl or haloalkyl having from 1 to 4 carbon atoms;
R** is methyl, ethyl, butyl, acetoxy methoxy, ethoxy or butoxy;
R is methyl, ethyl, butyl, methoxy, ethoxy, butoxy, or trimethylsiloxy;
R' is methyl, methoxy, ethoxy, butoxy or trimethylsiloxy;
R'' is methoxy, ethoxy, butoxy, trimethylsiloxy or vinyldimethylsiloxy;
R''' is methyl, ethyl, butyl or trimethylsilyl;
Me is methyl;
Z is methyl or W;
Q is an $NC_2CH_2-$, $NH_2CH_2CH_2NHCH_2-$, $NC-$, $HS-$ or $HSCH_2CH_2S-$ group;
n is an integer having a value of from 2 to 5;
m is an integer having a value of zero or one;
x is an integer having a value of from 1 to 100; and
y is an integer having a value of from 1 to 100.

Subgeneric to (I) are the compounds represented by the following subgeneric formulas:

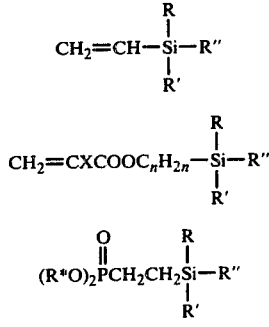

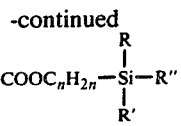

Subgeneric to (II) are the compounds represented by the following subgeneric formulas:

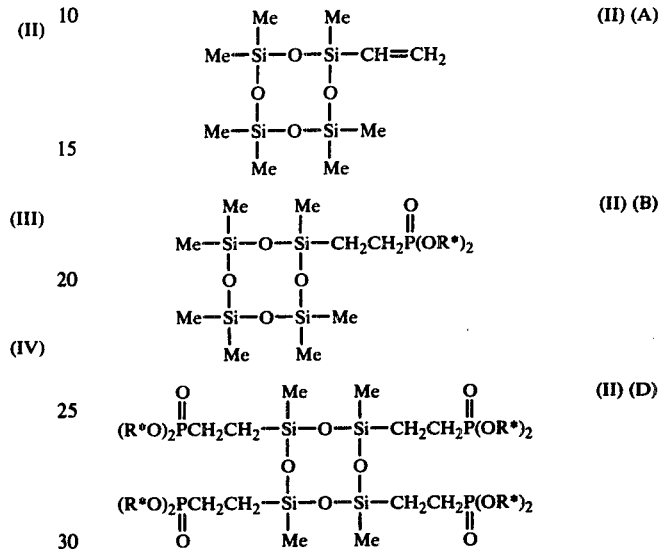

Illustrative of suitable silicon compounds one can mention the following: beta-cyanoethyl triethoxysilane, gamma-mercaptopropyl triethoxysilane, gamma-aminopropyl triethoxysilane, diethoxyphosphorylethyl methyl diethoxysilane, vinyl triethoxysilane, vinyl trimethoxysilane, vinyl triacetoxysilane, gamma-methacryloxypropyl trimethoxysilane, diethoxyphosphorylethyl heptamethyl cyclotetrasiloxane, trimethyl silyl terminated copolymer having dimethylsiloxy and methylvinylsiloxy units in the molecule, beta-cyanoethyl trimethylsilane, gamma-(2-aminopropyl triethoxysilane, S-beta(2-mercaptoethyl) mercaptoethyl triethoxysilane, beta-mercaptoethyl triethoxysilane, vinyl methyl diethoxysilane, vinyl methyl di(trimethylsiloxy)silane, tetramethyl divinyl disiloxane, heptamethyl vinyl cyclotetrasiloxane, 1,3,5,7-tetramethyl 1,3,5,7-tetravinyl cyclotetrasiloxane, diethoxyphosphorylethyl methyl diethoxysilane, diethoxyphosphorylisopropyl triethoxysilane, diethoxyphosphorylethyl methyl di(trimethylsiloxy)silane, heptamethyl diethoxyphosphorylethyl cyclotetrasiloxane, 1,3,5,7-tetramethyl 1,3,5,7-tetra(diethoxyphosphorylethyl)cyclotetrasiloxane, 1,1,3,3-tetramethyl-1,3-di(ethoxyphosphorylethyl)-disiloxane.

In a typical reaction, the prescribed amounts of dicarboxylic acid compounds, diols, modifiers and catalysts are charged to the reactor. The reaction mixture is then heated in an inert gas atmosphere at a temperature of from 180° C. to 210° C. to effect the initial esterification or transesterification. Thereafter, any excess glycol is removed and the transesterification is completed by heating the reaction mixture at a temperature of from about 225° C. to about 235° C. The second stage polycondensation reaction is then carried out by heating the reaction mixture at a temperature of from about 225° C. to about 325° C. under a reduced pressure of from about 0.1 mm. to about 20 mm. of mercury, preferably below about 1 mm. The use of the catalyst complexes or mixtures of this invention has often resulted in shorter overall reaction periods and decreased formation of glycol dimer, e.g. diethylene glycol.

The following examples serve to further illustrate the invention.

PREPARATION OF COORDINATION COMPLEXES

Example 1

A coordination complex was produced by preparing a solution of 19 grams of titanium tetrachloride in 60 ml. of dry benzene in a reaction flask and then adding thereto over a 30 minutes period 29.8 grams of diethoxyphosphorylethyl methyl diethoxysilane. The reaction was exothermic and a temperature of 60° C. was reached. It was stirred for one hour without temperature control and then the benzene was distilled in vacuo. The 1:1 molar ratio coordination complex was an oily liquid that weighed 48.8 grams. Microanalysis without further purification showed 28.08% Cl and 5.98% P.

Example 2

A solution of 4.75 grams of titanium tetrachloride in 60 ml. of dry benzene was prepared in a reactor. There was added thereto over a 30 minutes period 10.85 grams of cyanoethyl triethoxysilane with agitation at 25° C. The reaction was exothermic. After stirring at 25° C. for an additional hour the benzene was distilled in vacuo. The 1:2 molar ratio coordination complex was a yellow, oily liquid that weighed 15.6 grams. Microanalysis without further purification showed 21.20% Cl, 9.11% Si, 4.27% N and 8.77% Ti.

Example 3

A mixture of 4.56 grams of antimony trichloride and 36 grams of dry benzene was prepared in a reactor. To this mixture there was added at 25° C. over a 30 minutes period 41.8 grams of diethoxyphosphorylethyl methyl diethoxysilane. The reaction was exothermic. After stirring for an additional hour the benzene was removed in vacuo. The 1:7 molar ratio coordination complex was an oily liquid that weighed 46.4 grams.

Example 4

A solution of 6.5 grams of titanium tetrachloride in 30 ml. of dry benzene was slowly added to a stirred solution of 9.7 g. of diethoxyphosphorylethyl methyl diethoxysilane in 30 ml. of dry benzene. An exothermic reaction occurred and after standing for one hour the mixture was vacuum stripped at 30° C. The 1:1 molar ratio coordination complex was recovered as a residual red oil weighing 16.2 grams. A 1.4 grams portion of this complex was added to 1.8 grams of ethylene glycol at room temperature and the mixture was stirred until it became a homogeneous solution.

Example 5

A solution of 10.7 grams of germanium tetrachloride in 25 ml. of dry benzene was added over a period of 30 minutes to 22.1 grams of gamma-aminopropyl triethoxysilane. An exothermic reaction was observed. After stirring one hour without temperature control the benzene was distilled in vacuo. The 1:2 molar ratio complex was a white crystalline material weighing 33.2 grams.

Example 6

To a solution of 32.8 grams of diethoxyphosphorylethyl triethoxysilane in 50 ml. of dry benzene there was added a suspension of 11.66 grams of zirconium tetrachloride in 30 ml. of dry benzene. An exothermic reaction was observed. The mixture was stirred for one hour without temperature control after completion of the addition, filtered and stripped in vacuo. A colorless, odorless, oily 1:2 molar ratio coordination complex was obtained as a residue product; it weighed 43.9 grams.

Example 7

A solution of 13 grams of tin tetrachloride in 30 ml. of anhydrous benzene was slowly added to a solution of 14.99 grams of diethoxyphosphorylethyl methyl diethoxysilane in 30 ml. of dry benzene. An exothermic reaction was observed. After standing at room temperature for 20 hours the benzene was distilled in vacuo. The 1:1 molar ratio coordination complex was obtained as a yellow oil weighing 28 grams.

Example 8

A solution of 9.5 grams of titanium tetrachloride in 30 ml. of dry benzene was added slowly to a solution of 22.4 grams of beta-mercaptoethyl triethoxysilane in 50 ml. of dry benzene. An exothermic reaction was observed. After standing for 30 minutes the benzene was distilled in vacuo. The 1:2 molar ratio coordination complex, weighing 32.1 grams, was recovered as an orange, oily residue product.

In a similar manner the coordination complexes can be produced using zinc chloride, lead chloride or bismuth chloride in place of the titanium tetrachloride.

Example 9

(A) a mixture of 39.8 g. of dimethyl terephthalate, 34.1 grams of ethylene glycol, 0.0167 gram of the 1.1 coordination complex catalyst initially produced in Example 4 without addition of ethylene glycol and 0.0192 gram of zinc acetate dihydrate was heated at 178° to 186° C. for 3 hours under argon. During this first stage transesterification reaction methanol was distilled from the reactor. The temperature was raised to about 230° C. and maintained for one hour to complete the transesterification. Thereafter the temperature was raised to about 280° C. while the pressure was reduced to below 1 mm. of mercury and the second stage polycondensation reaction was carried out. During the polycondensation, samples of the polyester were removed at various times and intrinsic viscosity determined. The reaction was terminated when the intrinsic viscosity was 0.57, a typical value for commercially acceptable polyesters, and the time required was recorded as the polycondensation time (the time from reaching 1 mm. of mercury pressure to when the polyester has an intrinsic viscosity of 0.57). In this example the polycondensation time was 40 minutes. The intrinsic viscosity determinations reported in this application were obtained by preparing a solution of 0.5 weight percent of the polyester in O-chlorophenol and measuring its viscosity at 25° C. in an Ubbelohde viscometer.

(B) For comparison purposes, the polyester was produced using 39.4 grams of dimethyl terephthalate and 32.2 grams of ethylene glycol under temperature and pressure conditions similar to those described in Part A, supra. However, the catalyst used was the conventional catalyst, namely, 0.0179 gram of zinc acetate dihydrate as transesterification catalyst and 0.003 gram of antimony oxide as condensation catalyst. In this instance the polycondensation time was 75 minutes.

(C) In another reaction under the same reaction conditions but different catalyst concentrations than those stated in Part B, the polyester was produced using 0.0172 gram of zinc acetate dihydrate and 0.0186 gram of antimony oxide. In this instance the polycondensation time was 60 minutes.

Example 10

One of the undesirable side reactions during the polyesterification reaction is the formation of diethylene glycol. It is undesirable for at least two reasons, it is a by-product that cannot be recycled per se and it copolymerizes. Further, if too much of the diethylene glycol formed reacts in the condensation reaction it results in polyesters having lower melting points than desired. In this example it is shown that less diethylene glycol is produced using the coordination complexes of our invention as condensation catalyst.

(A) A mixture of 44.9 grams of dimethyl terephthalate, 35.3 grams of ethylene glycol and 0.0177 gram of the 1:1 coordination catalyst of Example 1 was reacted at 174° to 190° C. for 3 hours under argon and then at about 230° C. for one hour to complete the transesterification. Thereafter the polycondensation was carried out at 276° to 288° C. at a pressure below 1 mm. of mercury for a polycondensation time of 40 minutes. The polyester was white and had an intrinsic viscosity of 0.57.

A portion of the polyester was hydrolyzed and the amount of diethylene glycol in the polyester was determined by gas chromatographic analysis. The analysis indicated that 0.8 weight percent of the ethylene glycol that had dimerized to diethylene glycol had polycondensed.

(B) Following the same procedure described in Part A, but using 0.0186 gram of zinc acetate dihydrate and 0.02 gram of antimony oxide, a polyester having the same viscosity was obtained from an initial charge of 39.5 grams of dimethyl tetephthalate and 32.8 grams of ethylene glycol after a polycondensation time of 75 minutes.

Analysis of a portion of the polyester of this run (B) indicated that the polyester contained 1.81 weight percent of diethylene glycol; an amount 2.25 times the amount present in Part A, supra.

Example 11

The effect of a dyeability modifier on fiber color was examined in polymerizations using our novel coordination complexes and the prior conventional catalysts.

(A) Following the procedure described in Example 9, a mixture of 735.8 grams of dimethyl terephthalate, 534.2 grams of ethylene glycol, 0.2663 gram of zinc acetate dihydrate and 0.2622 gram of the 1:7 coordination complex catalyst of Example 3 was reacted to produce 605 grams of a polyester having an intrinsic viscosity of 0.5. The unmodified poly(ethylene terephthalate was very light yellow in color.

(B) A portion of the polyester of Part A was modified with 5 weight percent of poly[isopropyliminobis(trimethylene)succinate], a dyeability modifier. The modifier was added to the molten mass in the extruder of the spinnerette at 280° C. The modified polyester showed no color change after 30 minutes at that temperature in the extruder.

(C) The procedure of Part A was repeated using 736.4 grams of dimethyl terephthalate and 533.2 grams of ethylene glycol and a conventional catalyst system of 0.2711 gram of zinc acetate dihydrate and 0.2726 gram of antimony oxide to produce 541 grams of a white unmodified polyester.

(D) The procedure of Part B was repeated using the polyester of Part C. The modified polyester had changed to a grey color.

The spinning procedure used to produce fibers from the four mixtures, A to D above, is set forth below. The difference between A and C and B and D being the addition of the dyeability modifier to B and D as indicated in B.

The polyester was ground to a powder and vacuum dried for 24 hours before spinning. The molten polyester resin was forced through a sand-bed filter at 290° C. to remove gel particles and then extruded through a spinnerette having 30 holes, each 0.02 inch in diameter at a takeup velocity of 550 feet per minute. The tow was stretched by heating over a hot shoe and a heated pin at 95° C. The stretch ratio was about 4.5:1. In B and D the dyeability modifier was added as indicated.

The fibers had the following properties:

| Part | Color | Denier | Elongation at Break,% | Tenacity g/d. |
|------|-------|--------|----------------------|---------------|
| (A)  | White | 116    | 9.4                  | 4.9           |
| (B)  | White | 127    | 17.0                 | 3.5           |
| (C)  | White | 111    | 8.0                  | 4.3           |
| (D)  | Grey  | 120    | 14.0                 | 3.6           |

The data shows that the modified polyester (B) produced with the metal coordination complex catalysts of this invention was of better quality and stability, white vs. grey, than was the modified polyester (D) produced using the conventional catalyst system.

Example 12

Following the procedure similar to that described in Example 9, a mixture of 50.1 grams of dimethyl terephthalate, 42.7 grams of ethylene glycol, 0.0163 gram of zinc acetate dihydrate and 0.048 gram of the catalyst solution of Example 4 was reacted. The polycondensation time required to produce a white polyester having an intrinsic viscosity of 0.57 was only 24 minutes.

In Part A of Example 9, which used the coordination complex catalyst of Example 1, the same viscosity was achieved after a polycondensation time of 40 minutes. The coordination complex of Example 1 was not pretreated with ethylene glycol as was a portion of the coordination complex of Example 4. The data shows that pretreatment increased the activity and only 60% as much time (24 minutes) was required in Example 12 to produce a polyester having the same viscosity.

In Part C of Example 9, which used the conventional zinc acetate-antimony oxide catalyst, the same viscosity was achieved after a polycondensation time of 60 minutes. The data shows that the ethylene glycol pretreated catalyst solution of Example 4 increased the activity and only 40% as much time (24 minutes) was required to produce a polyester of the same viscosity.

Example 13

Following the procedure similar to that described in Example 9, a mixture of 39.7 grams of dimethyl terephthalate, 32.5 grams of ethylene glycol, 0.0181 gram of zinc acetate dihydrate and 0.0195 gram of the coordination complex catalyst of Example 5 was reacted. The polycondensation time required to produce a white polyester having an intrinsic viscosity of 0.57 was 30 minutes.

Following the same procedure, a larger batch was prepared using 736 grams of dimethyl terephthalate, 542 grams of ethylene glycol, 0.2747 gram of zinc acetate dihydrate and 0.303 gram of the same germanium coordination complex, 542 grams of ethylene glycol. The polyester was extruded to fiber-form as set forth in Example 11. The fibers had a denier of 126, an elongation at break of 16.1% and a tenacity of 3.99 g/d.

Example 14

Following the procedure of Example 9, a mixture of 736 grams of dimethyl terephthalate, 542.9 grams of ethylene glycol, 0.27 gram of zinc acetate dihydrate and 0.23 gram of the coordination complex catalyst of Example 7 was reacted. The polyester was white and had an intrinsic viscosity of 0.55. Fibers were produced as described in Example 11. The fibers had a denier of 101, an elongation at break of 9.7% and a tenacity of 4.8 g/d.

Example 15

Following the procedure of Example 9, a mixture of 38.8 grams of dimethyl terephthalate, 31.2 grams of ethylene glycol, 0.012 gram of zinc acetate and 0.02 gram of the coordination complex of Example 6 was reacted to produce a polyester having an average molecular weight of about 12,500 after a polycondensation period of about 90 minutes.

What we claim is:

1. A coordination complex of:
   (A) a metal halide of a metal selected from the group consisting of titanium, zirconium, zinc, germanium, tin, lead, antimony and bismuth; and
   (B) a silicon compound selected from the group consisting of:

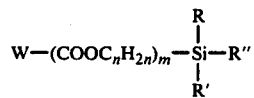  (I)

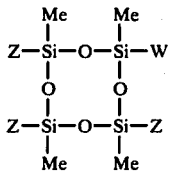  (II)

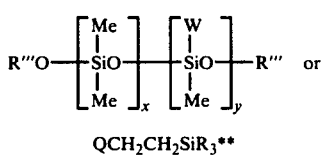  (III)

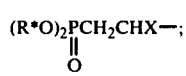  (IV)

wherein
W is CH$_2$=CX— or (R*O)$_2$PCH$_2$CHX—;
‖
O

X is hydrogen or methyl and is methyl only when m is one;
R* is alkyl or haloalkyl having from 1 to 4 carbon atoms;
R** is methyl, ethyl, butyl, methoxy, ethoxy or butoxy;
R is methyl, ethyl, butyl, methoxy, ethoxy, butoxy or trimethylsiloxy;
R' is methyl, methoxy, ethoxy, butoxy or trimethylsiloxy;
R" is methoxy, ethoxy, butoxy, trimethylsiloxy or vinyldimethylsiloxy;
R''' is methyl, ethyl, butyl or trimethylsilyl;
Me is methyl;
Z is methyl or W;
Q is NH$_2$CH$_2$—, NH$_2$CH$_2$CH$_2$NHCH$_2$—, NC—, HS— or HSCH$_2$CH$_2$S— group;
n is an integer having a value of from 2 to 5;
m is an integer having a value of zero or one;
x is an integer having a value of from 1 to 100; and
y is an integer having a value of from 1 to 100;
wherein the mole ratio of A:B in said coordination complex is from 1:1 to 1:7.

2. A coordination complex as claimed in claim 1, wherein silicon compound (B) is a compound of the general formula:

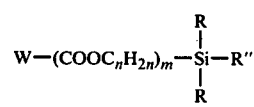

wherein W, R, R', R", n and m are as defined in claim 1.

3. A coordination complex as claimed in claim 1, wherein silicon compound (B) is a compound of the general formula:

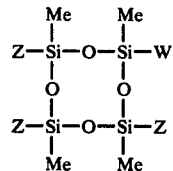

wherein Me, W and Z are as defined in claim 1.

4. A coordination complex as claimed in claim 1, wherein silicon compound (B) is a compound of the general formula:

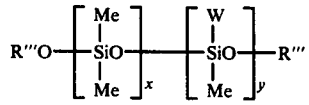

wherein Me, W, R''', x and y are as defined in claim 1.

5. A coordination complex as claimed in claim 1, wherein silicon compound (B) is a compound of the general formula:

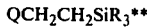

wherein Q and R** are as defined in claim 1.

6. A coordination complex as claimed in claim 1, wherein the silicon compound (B) is diethoxyphosphorylethyl methyl diethoxysilane.

7. A coordination complex as claimed in claim 1, wherein the silicon compound (B) is 3-aminopropyl triethoxysilane.

8. A coordination complex as claimed in claim 1, wherein the silicon compound (B) is 2-cyanoethyl triethoxysilane.

9. A coordination complex as claimed in claim 1, wherein the silicon compound (B) is 2-mercaptoethyl triethoxysilane.

10. A coordination complex as claimed in claim 1 of titanium tetrachloride and diethoxyphosphorylethyl methyl diethoxysilane.

11. A coordination complex as claimed in claim 1 of titanium tetrachloride and 2-cyanoethyl triethoxysilane.

12. A coordination complex as claimed in claim 1 of antimony trichloride and diethoxyphosphorylethyl methyl diethoxysilane.

13. A coordination complex as claimed in claim 1 of germanium tetrachloride and 3-aminopropyl triethoxysilane.

14. A coordination complex as claimed in claim 1 of zirconium tetrachloride and diethoxyphosphorylethyl methyl diethoxysilane.

15. A coordination complex as claimed in claim 1 of tin tetrachloride and diethoxyphosphorylethyl methyl diethoxysilane.

* * * * *